(12) United States Patent
Wright et al.

(10) Patent No.: US 12,329,367 B2
(45) Date of Patent: Jun. 17, 2025

(54) FLUID MIXING AND DELIVERY INJECTOR SYSTEM

(71) Applicants: Kenneth W Wright, Redondo Beach, CA (US); Matthew W Wright, Shaker Heights, OH (US)

(72) Inventors: Kenneth W Wright, Redondo Beach, CA (US); Matthew W Wright, Shaker Heights, OH (US)

( * ) Notice: Subject to any disclaimer, the term of this patent is extended or adjusted under 35 U.S.C. 154(b) by 391 days.

(21) Appl. No.: 18/074,389

(22) Filed: Dec. 2, 2022

(65) Prior Publication Data

US 2024/0180538 A1 Jun. 6, 2024

(51) Int. Cl.
 *A61B 17/00* (2006.01)
(52) U.S. Cl.
 CPC .......... *A61B 17/00491* (2013.01); *A61B 2017/00495* (2013.01)
(58) Field of Classification Search
 CPC ... A61B 17/00491; A61B 2017/00495; A61M 3/00; A61M 3/005; A61M 5/19; A61M 5/2066; A61M 5/2448; A61M 5/284; A61M 5/31596; A61M 5/3294
 See application file for complete search history.

(56) References Cited

U.S. PATENT DOCUMENTS

| | | | |
|---|---|---|---|
| 3,223,083 A | 12/1965 | Cobey | |
| 4,109,653 A | 8/1978 | Kozam et al. | |
| 4,359,049 A | 11/1982 | Redl et al. | |
| 4,631,055 A | 12/1986 | Redl et al. | |
| 4,842,581 A | 6/1989 | Davis | |
| 4,874,368 A | 10/1989 | Miller et al. | |
| 4,978,336 A | 12/1990 | Capozzi et al. | |
| 4,979,942 A | 12/1990 | Wolf et al. | |
| 5,104,375 A | 4/1992 | Wolf et al. | |
| 5,116,315 A | 5/1992 | Capozzi et al. | |
| 6,783,514 B2 | 8/2004 | Tovey et al. | |
| 10,959,714 B2 | 3/2021 | Guo et al. | |
| 11,253,391 B2 | 2/2022 | Grover et al. | |
| 2017/0182470 A1 | 6/2017 | Delmotte | |

*Primary Examiner* — Ryan J. Severson

(57) ABSTRACT

A fluid mixing and delivery system including a fluid injector to receive first and second fluids to be mixed together so that the resultant mixture can be delivered to a target site. The injector has particular application for introducing two fluid adhesive reagents to one another to produce a biomedical glue suitable to seal or plug a skin graft, wound, tear or minor break in the tissue or bone of a patient. The injector has a proximal end at which to receive the first and second fluids under pressure and a distal end at which the first and second fluids are mixed together within a common canal and expulsed therefrom by way of an exit tip. The common canal has a diameter that expands from narrow to wide in the direction of the mixture flowing therethrough to create a Per de Lavel anti-clogging nozzle and a Venturi effect at the exit tip so as to avoid a bottle neck blockage.

25 Claims, 9 Drawing Sheets

FLUID MIXING AND DELIVERY INJECTOR SYSTEM

BACKGROUND OF THE INVENTION

1. Field of the Invention

This invention relates to a fluid mixing and delivery injector system having particular application for mixing together two fluid adhesive reagents and producing a resultant biomedical glue to be delivered to a target site at which to seal or plug a tissue tear, secure a skin graft, close a wound, provide homeostasis, or repair a break in a patient's bone or tissue. The system includes a fluid injector having receptacles for receiving syringes or the like and individual fluid canals that join a common canal within which the adhesive reagents are mixed together, and the resultant glue is expulsed from an exit tip thereof. The common canal has a continuously expanding diameter from narrow to wide in the direction of the fluid flowing therethrough towards the exit tip to create a Per de Lavel nozzle and a Venturi effect so as to avoid clogging and enable the free flow of the glue therefrom. In a first embodiment, the individual fluid canals join the divergent common canal at the proximal end of the injector for creating collision and the mixing of the fluid reagents from the individual canals. In a second embodiment, the fluid injector has at least first and second upsloping fluid deflectors that project into the divergent common canal by which the fluid reagents are deflected towards one another and mixed together within the common canal. In a third embodiment, the divergent common canal is located at the distal end of the injector adjacent the exit tip and the individual canals are angled towards one another so that the fluid reagents collide and mix together in the common canal.

2. Background Art

There is a long felt need for a fluid injector that efficiently and completely combines and mixes two adhesive fluids to create a coagulated surgical tissue glue that flows freely out the injector without clogging or obstruction. Conventional fluid injectors are known to be unreliable because they are easily obstructed by upstream mixing of reagents and premature coagulation which may cause a "bottle neck" obstruction. An obstructed injector can expel a potentially dangerous projectile during a medical procedure.

In particular, some commercially available fluid injectors include a relatively large or wide mixing chamber which is joined to a smaller diameter canal or catheter. Mixing of the two adhesive components occurs in the mixing chamber and the mixture is forced into the narrow canal or catheter. Coagulated or semi-coagulated adhesive reagents are known to clog the relatively narrow catheter and the exit tip and thereby cause the "bottle neck" obstruction. Increased pressure is then required to push a viscous semi-coagulated or coagulated adhesive mixture through the narrow exit tip. The increased pressure that is applied to the injector to clear the obstruction from the tip may result in the ejection of a hard projectile. Such an obstruction can be dangerous in both medical and non-medical environments especially in a surgical setting.

To overcome the problem of the injector expelling an obstruction during the delivery of surgical tissue glue, many commercially available injectors are provided with a safety strap to hold the tip in place and avoid the expulsion of the obstruction. Also, primary and backup adhesive injectors are necessary should the primary injector become occluded and rendered unusable during a medical procedure.

Some conventional adhesive injectors employ two individual canals to supply adhesive reagents to be mixed together in a chamber that is coupled to a common canal having a constant size or a size that is the same as or smaller than the diameter of the individual canals. An injector configuration where the common canal has a constant diameter results in resistance to out flow and retrograde back flow of the reagents into one of the individual canals by which to cause upstream coagulation and obstruction of the injector. Other conventional adhesive injectors have parallel individual canals that exit separately at the distal aspect of the injector such that the individual reagents may not be adequately mixed together. Injectors that have individual canals aligned in a parallel orientation prior to their being joined to a common canal are known to provide laminar flow along the wall of the common canal which keeps the reagents separated rather than being mixed together.

SUMMARY OF THE INVENTION

In general terms, a fluid mixing and delivery system is described including a fluid injector having a pair of cylindrical fluid receiving receptacles at a proximal end thereof to receive therewithin first and second syringes or the like to supply first and second adhesive fluids under pressure to be mixed together to create a coagulative adhesive sealant. The fluid receiving receptacles communicate with respective fluid intake channels by which the first and second adhesive fluids are delivered to a common canal. The fluid intake channels are aligned with one another to make an orthogonal angle therebetween.

In a first fluid injector embodiment, the individual fluid intake channels are angled towards one another so as to intersect at a fluid junction. The fluid junction communicates with the common canal within which the first and second adhesive fluids collide and mix together. The common canal runs longitudinally through an anti-clogging applicator nozzle between the fluid junction and a beveled exit tip at the distal end of the fluid injector. The resultant adhesive mixture is a biomedical glue (e.g., Cyanoacrylic or Fibrin) that is expulsed from the beveled exit tip to be applied to a target site in order to seal or plug, for example, a skin graft, wound, tear or minor break in the tissue or bone of a patient.

The common canal within which the first and second fluid are mixed together has a divergent shape and a cross-sectional diameter that continuously increases towards the exit tip in the direction of the fluid flowing through the applicator nozzle. Moreover, the diameter of each of the cylindrical fluid receiving receptacles of the fluid injector is larger than the diameter of each of the fluid intake channels with which the fluid receiving receptacles communicate. Each of the fluid intake channels has a diameter which is smaller than the diameter of the common canal at the exit tip. This changing configuration of the fluid injector from the large diameter syringe receiving receptacles connected to the smaller diameter fluid intake channels which are connected to the larger diameter common canal creates a Per de Lavel nozzle and a Venturi effect resulting in a decreasing pressure gradient in the common canal towards the exit tip at the distal end of the injector so as to prevent backflow through the anti-clogging applicator nozzle and the fluid intake channels. Accordingly, an upstream coagulation and injector obstruction can be advantageously avoided to allow the free expulsion of the resultant glue mixture from the exit tip without the significant risk of a bottle neck blockage and the ejection of a projectile from the injector.

In a second embodiment, a fluid injector includes a pair of individual fluid canals having a constant diameter. The individual fluid canals run longitudinally and in parallel alignment with one another through the anti-clogging applicator nozzle between respective ones of the fluid intake channels and a larger diameter divergent common canal that is located at the distal end of the injector. The diameter of the divergent common canal expands in the direction of the flow of fluid therethrough towards the exit tip. At least first and second fluid deflectors project inwardly towards one another into the divergent common canal. The fluid deflectors are angled upwardly in the direction of the fluid flowing through the common canal. First and second adhesive fluids being carried by the fluid canals are directed against respective ones of the first and second upwardly angled fluid deflectors. The first and second adhesive fluids are thusly deflected towards one another to collide in the common canal where they are mixed together. Accordingly, a coagulated biomedical glue mixture is expulsed from the exit tip of the modified fluid injector to be applied to a target site by way of the divergent common canal.

In a third embodiment, a fluid injector includes a pair of individual fluid canals having a constant diameter. The individual fluid canals run longitudinally and in parallel alignment with one another through the anti-clogging applicator nozzle between respective ones of the fluid intake channels and a divergent common canal that is located close to the exit tip at the distal end of the injector. The diameter of the divergent common canal expands in the direction of the flow of fluid therethrough towards the exit tip. Each of the fluid canals is closed by an angled end wall that slopes upwardly in the direction of the fluid flow, and each of the end walls has a fluid aperture formed therein. First and second adhesive fluids being carried by respective ones of the fluid canals are angled towards one another by the apertures formed in the upsloping end walls such that the adhesive fluids intersect one another at a collision point within the common canal. The intersecting fluids are mixed together and a biomedical glue mixture is expulsed from the divergent common canal to the exit tip of the injector to be applied to a target site.

DESCRIPTION OF THE PREFERRED EMBODIMENT

Described below while referring concurrently to FIGS. 1-6 of the drawings is a fluid mixing and delivery injector system by which two fluid adhesive reagents are combined to create a coagulative adhesive sealant. The mixing and delivery injector system has particular application for delivering the adhesive sealant (i.e., a coagulated surgical tissue glue) to a target site in a medical environment such as, for example, to seal or plug a tissue tear, secure a skin graft, close a wound, provide homeostasis, or repair a break in a patient's bone or tissue.

Figure 1:
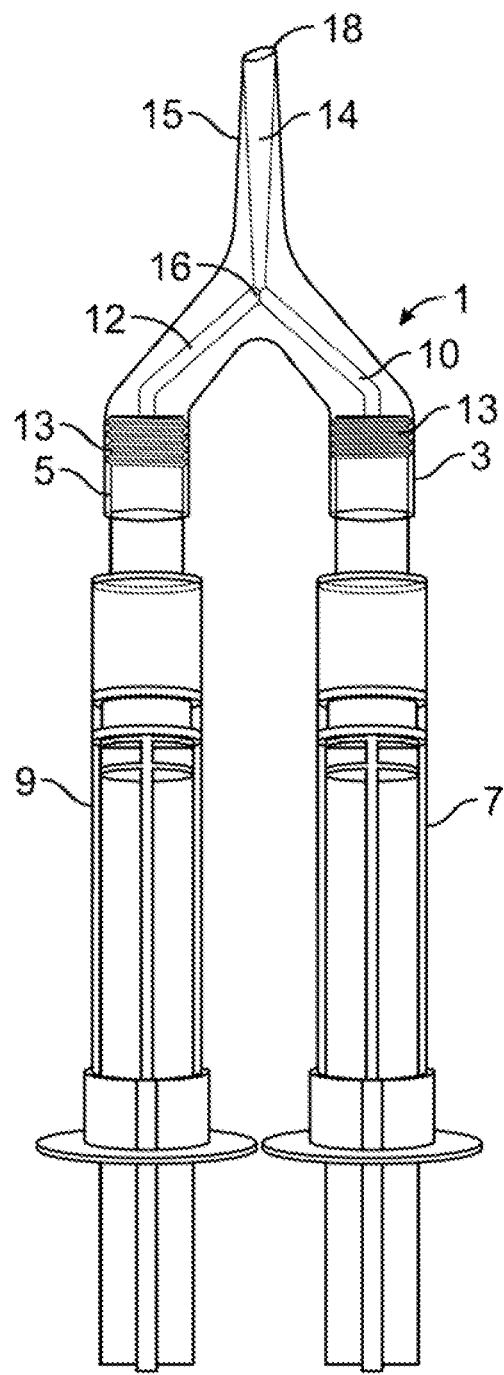
FIG. 1 shows a fluid mixing and delivery system including a fluid injector according to a first embodiment and a pair of syringes for supplying first and second adhesive fluids to the fluid injector within which the fluids are mixed together to create a coagulated glue adhesive to be delivered to a target site.

The mixing and delivery injector system includes a fluid injector 1 that is manufactured from a hard medical grade plastic, or the like. The proximal end of the injector 1 has a pair of cylindrical fluid receiving receptacles 3 and 5 at which to receive under pressure the first and second fluid adhesive reagents to be mixed together. One of the fluid adhesive reagents is a known hardening agent. By way of a preferred embodiment and as is best shown in FIG. 1, the fluid receptacles 3 and 5 at the proximal end of applicator 1 are configured to be coupled to large bore syringes 7 and 9 or any other suitable pressure generating fluid delivery device. To facilitate a reliable connection, each of the fluid receiving receptacles 3 and 5 is formed with a set of screw threads 13 (best shown in FIGS. 2 and 5) that bite into and lock the syringes 7 and 9 in place when the relatively soft tips of the syringes are rotated into the harder fluid receiving receptacles 3 and 5 of the injector 1. The fluid receiving receptacles 3 and 5 communicate with respective fluid intake channels 10 and 12. According to a first embodiment of this invention, the fluid intake channels 10 and 12 lie in fluid communication with a common canal 14 having a divergent diameter. The fluid intake channels 10 and 12 and the common canal 14 of the fluid injector 1 are arranged relative to one another in a Y-configuration.

Figure 2:
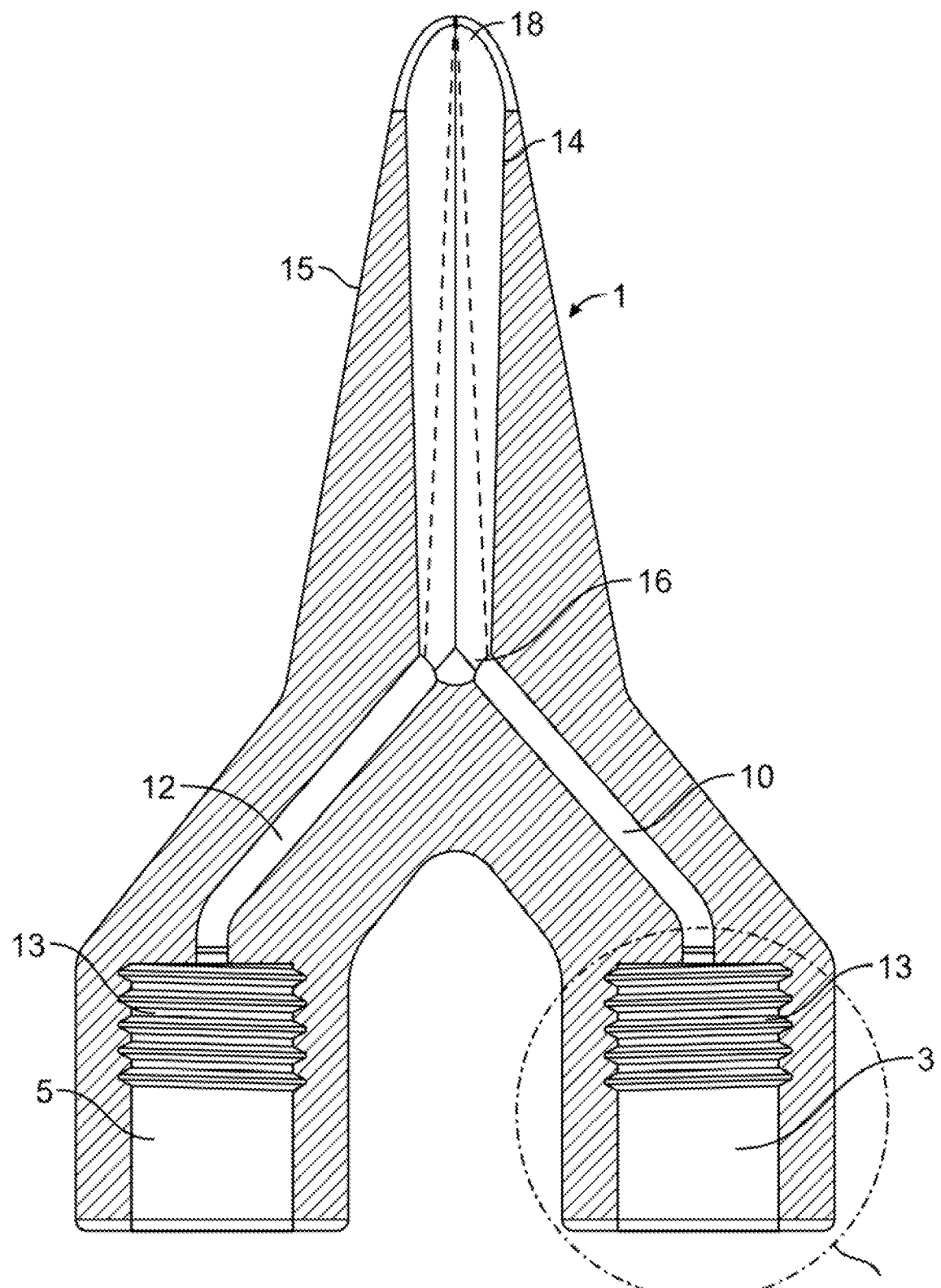
FIG. 2 is a cross-section of the fluid injector of the fluid mixing and delivery system shown in FIG. 1 having a divergent common canal running through an anti-clogging applicator nozzle thereof.

As is best shown in FIG. 2, the common canal 14 runs through an anti-clogging applicator nozzle 15 at the distal end of the fluid injector 1 from a fluid junction 16 where the fluid intake channels 10 and 12 are joined to one another and to the common canal 14. Pressure generated by depressing the plungers of the syringes 7 and 9 causes the fluid adhesive reagents carried by the syringes to be correspondingly pushed through the individual fluid intake channels 10 and 12 and into the divergent common canal 14 where the reagents are introduced to one another at the fluid junction 16 and mixed together within the common canal 14 by way of the fluid junction 16. The adhesive mixture is expulsed from the common canal 14 at an exit tip 18 thereof at the distal end of the fluid injector 1 so that the resultant coagulated glue can be delivered to a target site such as that of a patient.

As is best shown in FIG. 2, the diameter of each of the cylindrical fluid receiving receptacles 3 and 5 of the fluid injector 1 has a diameter that is larger than the diameter of each of the fluid intake channels 10 and 12, and each of the fluid intake channels 10 and 12 has a diameter that is smaller than the diameter of the divergent common canal 14 at the exit tip 18. By way of example only, the diameter of the fluid receiving receptacles 3 and 5 is about four times larger than the diameter of the fluid intake channels 10 and 12. The maximum diameter of the divergent common canal 14 at its exit tip 18 thereof is about 2.5 times larger than the diameter of each of the fluid intake channels 10 and 12.

As is also best shown in FIG. 2, the divergent common canal 14 of the fluid injector 1 has a diameter that expands through the applicator nozzle 15 from narrow to wide in the direction of the fluid flowing through the nozzle between the fluid junction 16 and the exit tip 18. The changing diameters through the fluid injector 1 from relatively wide (at the fluid receiving receptacles 3 and 5), to relatively small (at the fluid intake channels 10 and 12), and then back to relatively wide (within the divergent common canal 14) creates a Per de Lavel nozzle and a Venturi effect with a decreasing pressure gradient towards the exit tip 18 at the distal end of injector 1.

Accordingly, fluid pressure within the continuously expanding diameter of the divergent common canal 14 decreases as the fluid moves through the applicator nozzle 15 towards the exit tip 18 at the distal end of the injector 1 from the fluid receiving receptacles 3 and 5 at the opposite proximal end. The continuously expanding diameter of the common canal 14 reduces the pressure at the exit tip 18 and thereby advantageously prevents the backflow of fluid through the anti-clogging applicator nozzle 15 and into the fluid intake channel 10 and 12. That is to say, the pressure gradient changing progressively from high to low in the continuously expanding common canal 14 prevents retrograde back flow of fluid into the fluid intake channels 10 and 12. By virtue of the foregoing, an upstream coagulation and a corresponding obstruction can be better avoided. What is more, the continuously expanding diameter of the divergent common canal 14 allows for a free expulsion of the resultant mixture of the fluid adhesive reagents from the exit tip 18 without the significant risk of a bottle neck blockage that could occur in conventional injectors as a consequence of viscous semi-coagulated and coagulated combined reagents. As a further advantage, the divergent common canal allows for lower delivery pressure and out flow to provide better control of fluid delivery and prevent an abrupt uncontrolled spurting of fluid as is common with standard convergent or parallel nozzle configurations.

Figure 3:
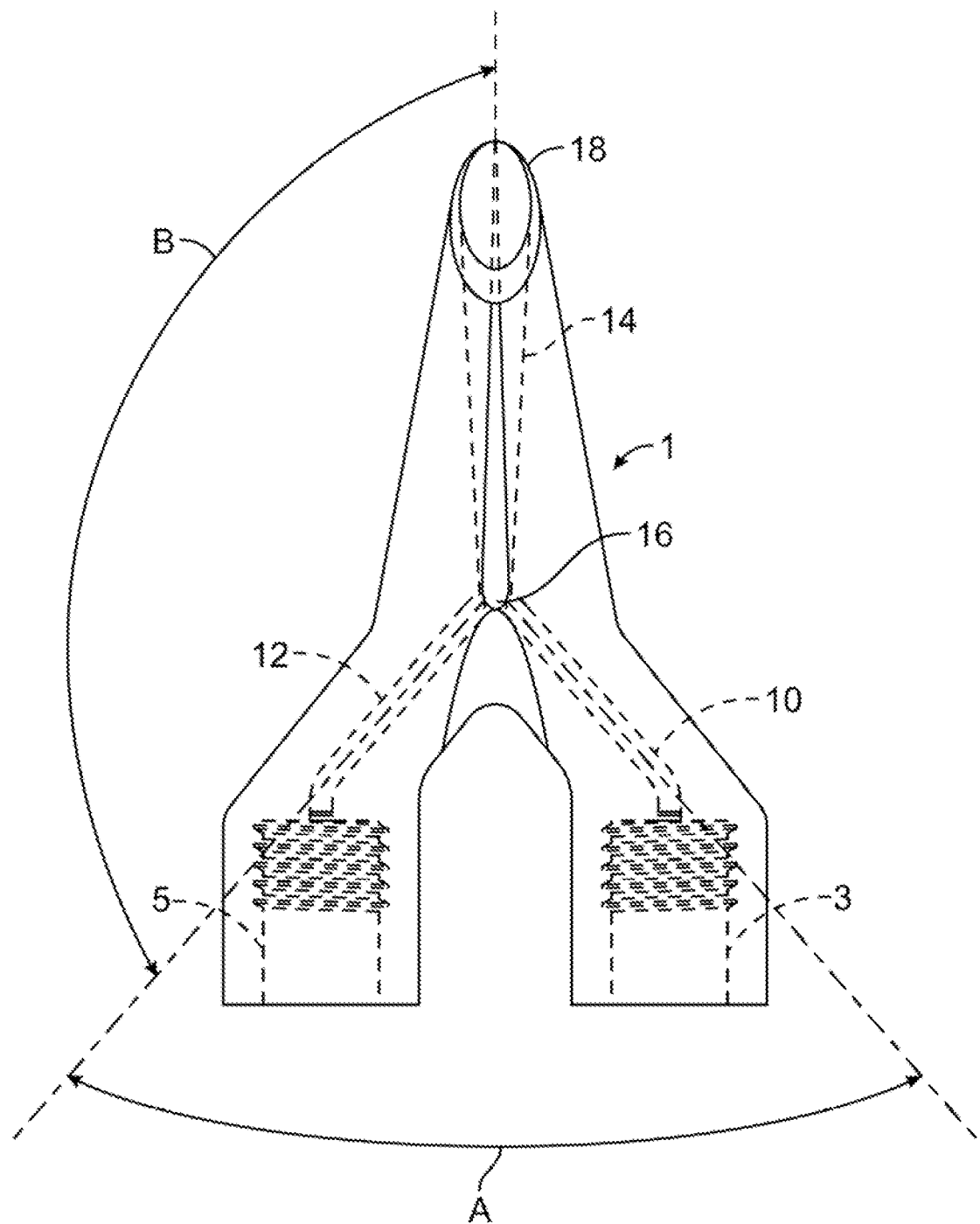
FIG. 3 illustrates the alignment of the adhesive fluid flow paths through the fluid injector of FIG. 2.

As is best shown in FIG. 3, the pair of fluid intake channels 10 and 12 that receive the fluid adhesive components from the fluid receiving receptacles 3 and 5 are orthogonally aligned with one another at an angle "A" so as to be joined to one another to produce a collision of the fluid components at the fluid junction 16. Moreover, the longitudinal axis of the common canal 14 is aligned with respective ones of the longitudinal axes of the orthogonally aligned fluid intake channels 10 and 12 so that an angle "B" of 135 degrees is formed therebetween in a Y-shaped orientation. This orientation of the fluid intake channels 10 and 12 with one another and with the common canal 14 maximizes the mixing and reaction actuation of the fluid adhesive within the common canal 14.

Figure 4:
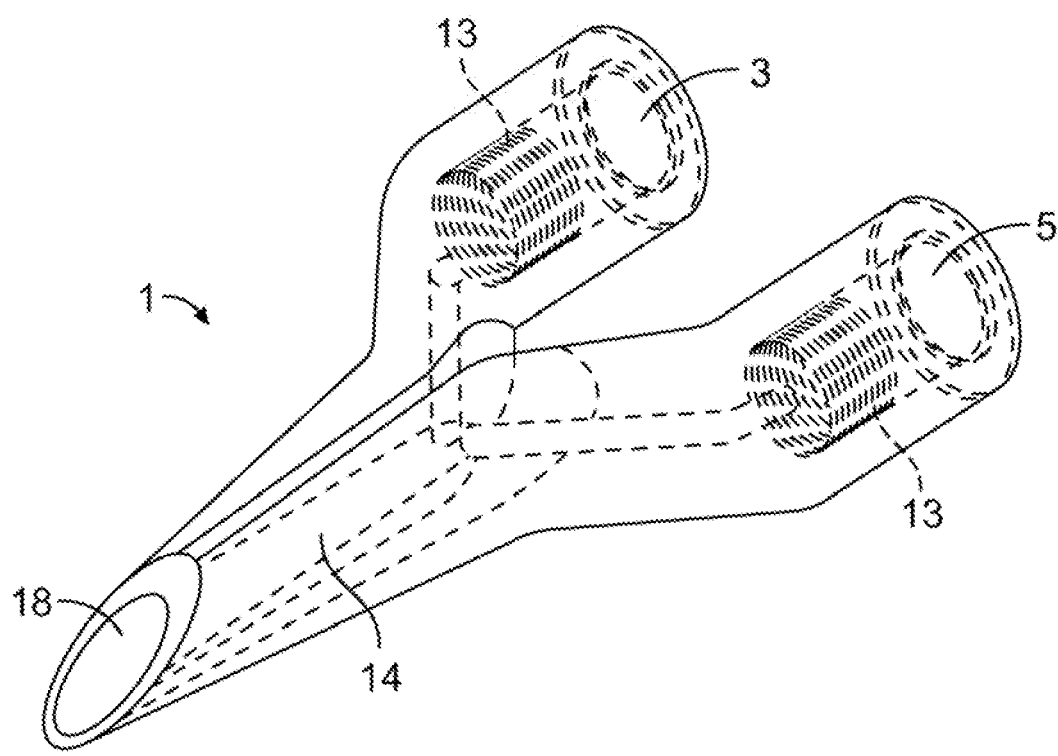
FIG. 4 is a perspective view of the fluid injector.
Figure 5:
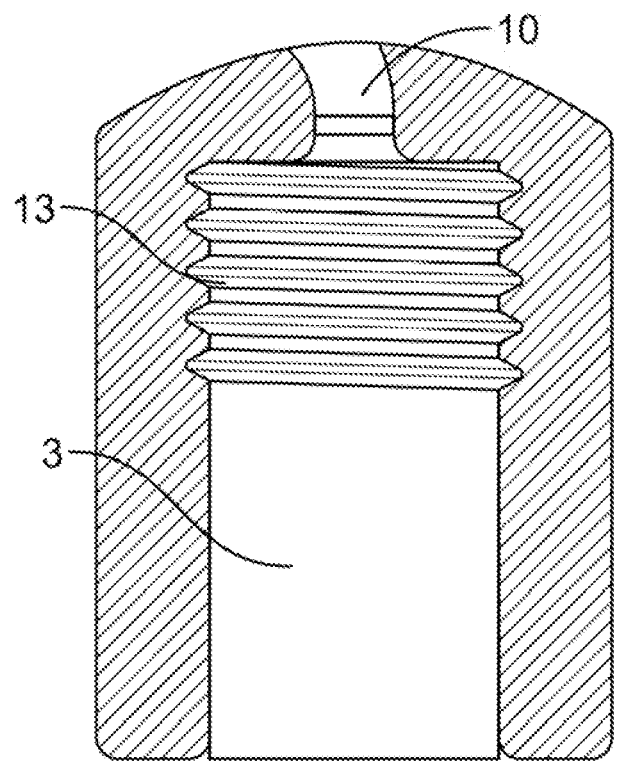
FIG. 5 is an enlarged detail of one adhesive fluid receiving receptacle of the fluid injector taken from FIG. 2.
Figure 6:
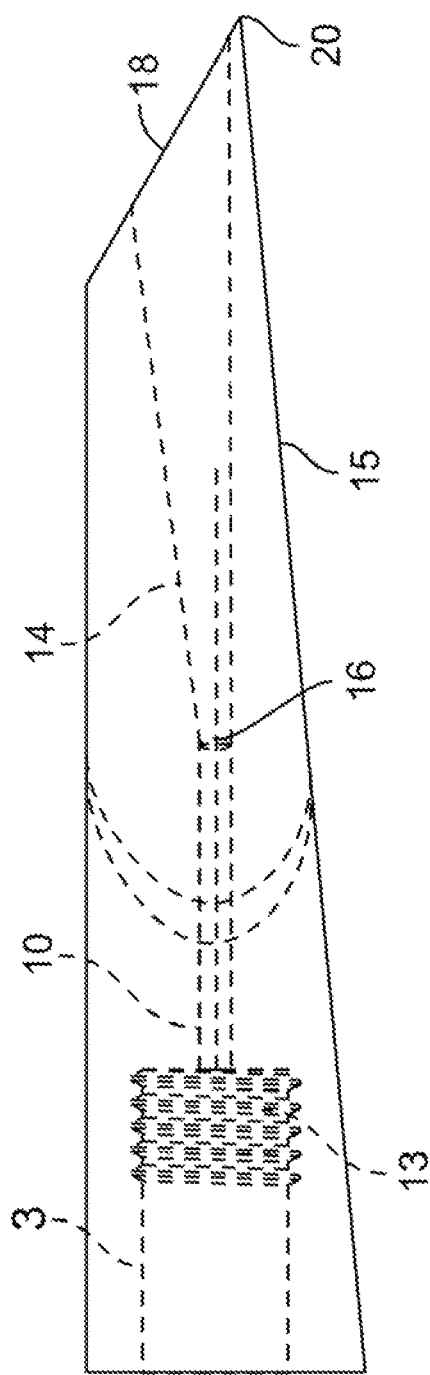
FIG. 6 is a side view of the fluid injector.

The velocity of the fluids flowing through the relatively narrow fluid intake channels 10 and 12 is higher than the velocity of the fluid flowing out of the relatively wide fluid receiving receptacles 3 and 5, whereby to increase the velocity of the adhesive components when they collide with one another at the fluid junction 16. Likewise, the velocity of the resultant fluid adhesive mixture that is expulsed from the injector at the exit tip 18 is correspondingly increased. In this same regard, and as is best shown in FIGS. 3, 4 and 6, the ideal exit tip 18 of the fluid injector 1 has a beveled configuration. The beveled exit tip 18 is angled so as to terminate at a sharp point 20 that facilitates the separation of overlaying tissue membranes of a patient to allow the insertion of tip 18 and the injection of the adhesive mixture between adjacent membrane layers. During the use of the fluid injector 1 in a medical environment, the beveled exit tip 18 is preferably positioned face down so as to lie against the patient's tissue by which a resultant biomedical glue (e.g., Cyanoacrylic or Fibrin) can be more widely and evenly spread at the intended target site in order to seal or plug a skin graft, wound, tear or minor break in the patient's tissue or bone. However, it should be understood that the exit tip 18 of injector 1 need not be beveled.

Figure 7:
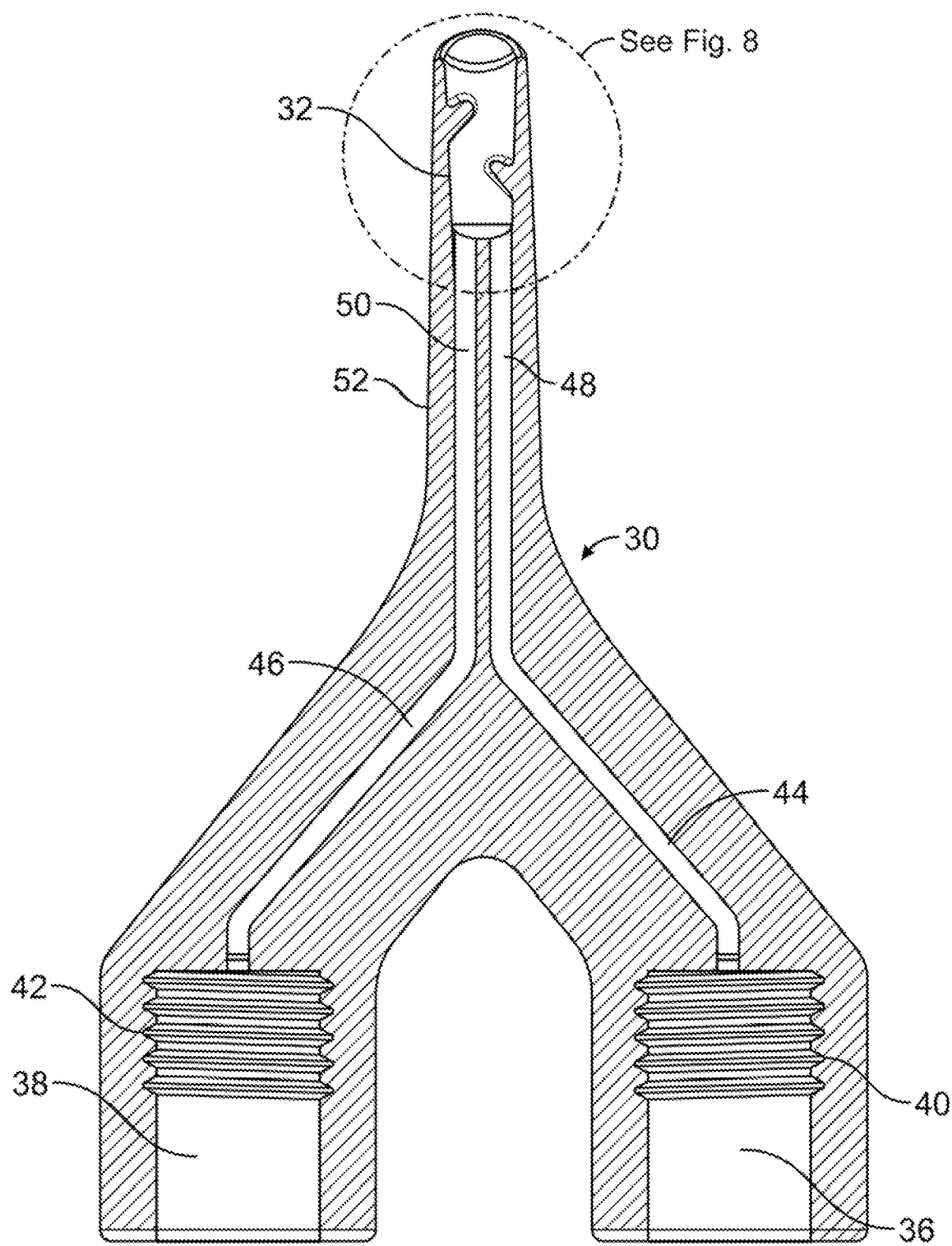
FIG. 7 shows a fluid injector according to a second embodiment wherein first and second adhesive fluids are deflected towards one another and mixed together by means of fluid deflectors that project into a divergent common canal to create a coagulated glue adhesive to be delivered to a target site.
Figure 8:
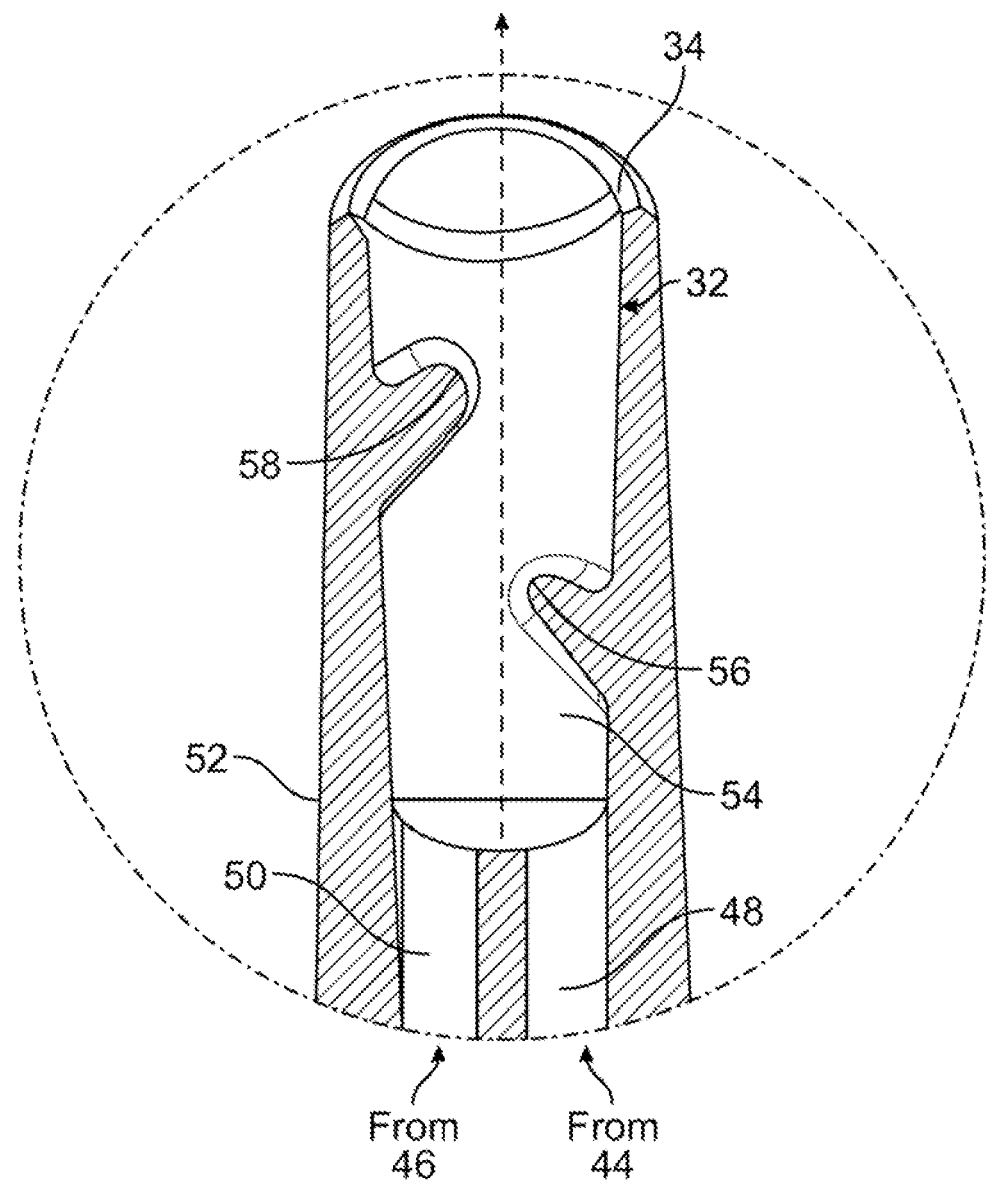
FIG. 8 is an enlarged detail of the divergent common canal of the fluid injector shown in FIG. 7.

FIGS. 7 and 8 of the drawings show a fluid injector 30 that includes a modification to the fluid injector 1 that was described while referring to FIGS. 1-6. As in the case of the fluid injector 1, two adhesive reagents are combined within a common canal 32 that is located adjacent the exit tip 34 at the distal end of the fluid injector 30. As also in the case of the fluid injector 1, the fluid injector 30 has a pair of cylindrical fluid receiving receptacles 36 and 38 at the proximal end thereof. A set of screw threads 40 and 42 runs around each of the receptacles 36 and 38 to bite into and hold a pair of syringes (not shown) or the like in place. The fluid receiving receptacles 36 and 38 communicate with respective fluid intake channels 44 and 46. When the plungers of the syringes are depressed, first and second fluid reagents carried by the syringes are supplied under pressure to the fluid intake channels 44 and 46 which lie in fluid communication with the fluid receiving receptacles 36 and 38.

According to a second fluid injector embodiment, each of the fluid intake channels 44 and 46 of the fluid injector 30 communicates with an individual fluid canal 48 and 50 having a constant diameter. The fluid canals 48 and 50 extend in spaced parallel alignment with one another through an anti-clogging applicator nozzle 52 and between the fluid intake channels 44 and 46 and the common canal 32 that lies adjacent the exit tip 34 at the distal end of the fluid injector 30.

Each of the individual fluid canals 48 and 50 supplies one of the two fluid adhesive reagents to the common canal 32. The common canal 32 of the fluid injector 30 has a longitudinally extending flow path 54 through nozzle 52 and a divergent diameter that expands continuously in the direction of the flow path 54 towards the exit tip 34. The diameter of the common canal 72 is larger than the constant diameter of the fluid canals 48 and 50.

At least first and second fluid deflectors 56 and 58 that lie opposite each other project inwardly towards one another within the common canal 32. However, it is to be understood that any suitable number of fluid deflectors can project into the common canal 32. Each of the fluid deflectors 56 and 58 is angled upwardly in the direction in which the fluids flow into and through the common canal 32. As is best shown in FIG. 8, the upsloping surfaces of the fluid deflectors 56 and 58 are preferably aligned with one another so that an orthogonal angle is formed therebetween.

The first fluid adhesive reagent that is carried under pressure by the first fluid canal 48 running through the anti-clogging applicator nozzle 52 is directed against the first fluid deflector 54 within the flow path 54 of the common canal 32. The second fluid adhesive reagent that is carried under pressure by the second fluid canal 50 running through the applicator nozzle 52 is directed against the second fluid deflector 58 within the flow path 54 of the common canal 32. By virtue of the upsloping surfaces of the angled fluid deflectors 56 and 58, the first and second fluid adhesive reagents that are delivered to the common canal 32 by the fluid intake channels 44 and 46 are deflected towards one another and mixed together in the common canal 32 to create a coagulated biomedical glue to be expulsed from the exit tip 34 of the fluid injector 30 to the target site.

The fluid pressure in the larger diameter divergent common canal 32 is less than the pressure in the individual smaller diameter fluid canals 48 and 50 so as to result in a decreasing pressure gradient as the fluid moves through the anti-clogging nozzle 52 to the exit tip 34. By virtue of the foregoing, retrograde back flow and upstream coagulation in the individual canals 48 and 50 can be avoided. The continuously expanding diameter along the flow path 54 of the common canal 32 allows the combined adhesive to flow freely out the exit tip 34 to avoid bottle neck injector obstruction by viscous semi-coagulated and coagulated combined reagents.

In the fluid injector 30 that is shown in FIGS. 7 and 8, a pair of fluid reagents are combined with one another within a common canal 32 of an applicator nozzle 52 that is located at the distal end of the injector. A pair of fluid deflectors 56 and 58 project from the applicator nozzle 52 into the common canal 32, whereby the pair of fluid reagents that flow through respective fluid canals 48 and 50 are deflected towards one another and mixed together so that the resultant mixture can be expulsed from the common canal 32 at the exit tip 34 of the injector.

Figure 9:
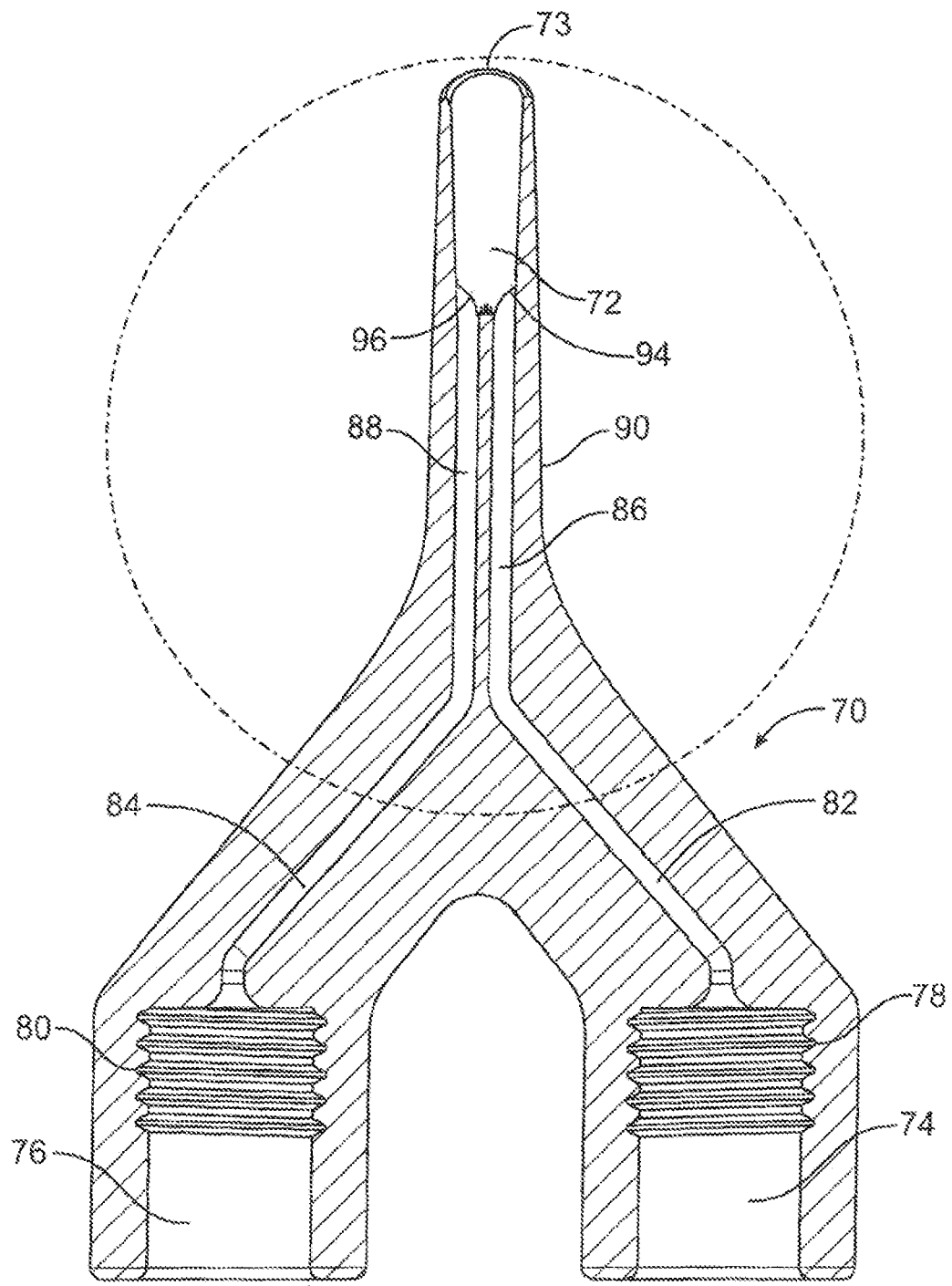
FIG. 9 shows a fluid injector according to a third embodiment wherein first and second adhesive fluids are angled towards one another and mixed together by way of individual fluid canals that extend into a divergent common canal at the distal tip of the injector to create a coagulated glue adhesive to be delivered to a target site.
Figure 10:
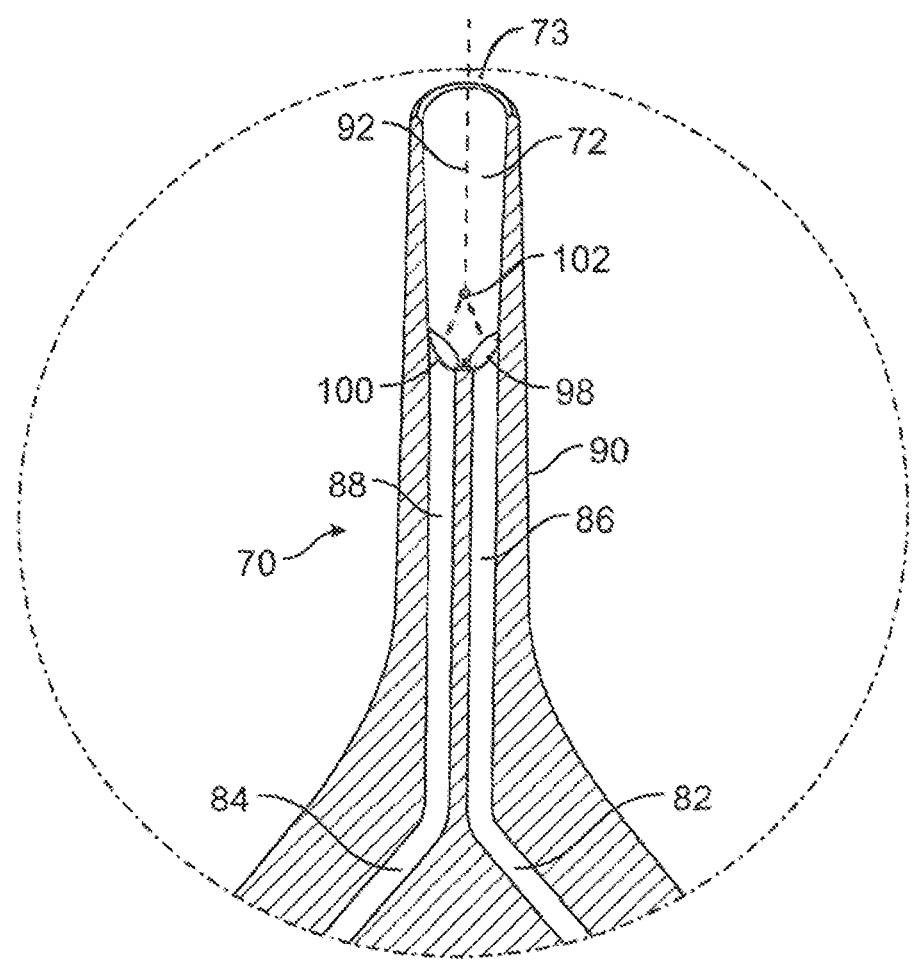
FIG. 10 is an enlarged detail of the divergent common canal of the fluid injector shown in FIG. 9.

FIGS. 9 and 10 of the drawings show a fluid injector 70 like that shown in FIGS. 7 and 8, but without the aforementioned fluid deflectors projecting into the common canal. Like the fluid injector 30, the fluid injector 70 preferably combines two adhesive reagents within a common canal 72 that is located close to the exit tip 73 at the distal end of the injector. Also like the fluid injector 30, the fluid injector 70 has a pair of cylindrical fluid receiving receptacles 74 and 76 at the proximal end thereof. A set of screw threads 78 and 80 runs around each of the receptacles 74 and 76 to bite into and hold a pair of syringes (not shown) or the like in place. The fluid receiving receptacles 74 and 76 communicate with respective fluid intake channels 82 and 84. When the plungers of the syringes are depressed, first and second fluid reagents carried by the syringes are supplied under pressure to the fluid intake channels 82 and 84 which lie in fluid communication with the fluid receiving receptacles 74 and 76.

The fluid intake channels 82 and 84 of the fluid injector 70 communicate with respective fluid canals 86 and 88 having a constant diameter. The individual fluid canals 86 and 88 extend in spaced parallel alignment with one another through an anti-clogging applicator nozzle 90 and between the fluid intake channels 82 and 84 and the common canal 72 at the distal end of the fluid injector 70.

Each of the individual fluid canals 86 and 88 supplies one of the two fluid adhesive reagents to the common canal 72. The common canal 72 of the fluid injector 70 has a longitudinally extending flow path 92 and a divergent diameter that expands in the direction of the flow path 92 through nozzle 90 towards the exit tip 73. The diameter of the common canal 72 is larger than the constant diameter of the fluid canals 86 and 88.

According to a third fluid injector embodiment, in place of the fluid deflectors 56 and 58 of the fluid injector 30, the distal ends of the fluid canals 86 and 88 of the fluid injector 70 are closed by angled end walls 94 and 96 of FIG. 9. As is best shown in FIG. 10, each end wall 94 and 96 has a fluid aperture 98 and 100 extending therethrough. The end walls 94 and 96 slope outwardly away from the common canal 72 and upwardly in the direction of the fluid flow through the applicator nozzle 90 such that the apertures 98 and 100 communicate with the common canal 72. The upsloping walls 94 and 96 of the fluid canals 86 and 88 are ideally aligned with one another such that an orthogonal angle is formed therebetween. By virtue of the upsloping end walls 94 and 96, the first and second fluid adhesive reagents that are carried under pressure to the applicator nozzle 90 by the individual fluid canals 86 and 88 are forced at an angle through the apertures 98 and 100 and into the common canal 72 so as to be directed towards one another and mixed together at a collision point 102 where the fluid reagents intersect. A coagulated biomedical glue mixture will therefore travel from the collision point 102 along the longitudinal flow path 92 through the common canal 72 of the applicator nozzle 90 to be delivered by way of the exit tip 73 of the fluid injector 70 to a target site.

It may be appreciated that the common canal 72 of the fluid injector 70 of FIGS. 9 and 10 is shorter than each of the common canals 14 and 32 of the injectors 1 and 30 of FIGS. 1-8. In particular, the length of the common canal 72 is less than one half the length of the non-clogging applicator nozzle 90 in which the common canal is located. In this case, the common canal 72 and the collision point 102 therewithin lie close to the distal exit tip 73 so that the pressure of the glue mixture being applied by way of the exit tip is maximized. It should also be understood that while the fluid injectors 1, 30 and 70 disclosed herein have a particular medical application for mixing an dispensing a biomedical glue, the injectors can also be used for mixing and dispensing other fluids in non-biomedical and non-adhesive applications.

The invention claimed is:

1. A fluid mixing and delivery injector having a proximal end at which to receive first and second fluids and a distal end at which the first and second fluids are mixed together so that the resultant mixture can be delivered to a target site, said fluid mixing and delivery injector comprising:
   first and second fluid receiving receptacles located at the proximal end of the injector at which the first and second fluids to be mixed together are received under pressure;
   first and second fluid input channels lying in fluid communication with respective ones of said first and second fluid receiving receptacles so as to receive the first and second fluids under pressure from said first and said second fluid receiving receptacles; and
   a common canal located at the distal end of said injector and lying in fluid communication with each of said first and second fluid input channels so that the first and the second fluids within said first and second fluid input channels are introduced to one another and mixed together within said common canal to be delivered to the target site, said common canal having a divergent diameter which increases from narrow to wide in the direction of the fluid flowing therethrough.

2. The fluid mixing and delivery injector recited in claim 1, wherein said common canal is joined to said first and second fluid input channels at a fluid junction lying therebetween.

3. The fluid mixing and delivery injector recited in claim 2, wherein said common canal has a divergent shape, such that the diameter of said common canal increases from narrow to wide in the direction of the fluid flowing therethrough starting at the fluid junction at which said common canal is joined to said first and second fluid input channels.

4. The fluid mixing and delivery injector recited in claim 1, wherein said common canal and said first and second fluid input channels are aligned with one another so as to have a Y-shaped configuration.

5. The fluid mixing and delivery injector recited in claim 1, wherein said first and said second fluid input channels are aligned with one another so that an orthogonal angle is formed therebetween.

6. The fluid mixing and delivery injector recited in claim 5, wherein each of said first and said second fluid input channels and said common canal has a longitudinal axis, said common canal and said first and said second fluid input channels positioned relative to one another in a Y-shaped configuration so that a 135 degree angle is formed between the longitudinal axis of said common canal and respective ones of the longitudinal axes of said first and said second fluid input channels.

7. The fluid mixing and delivery injector recited in claim 1, wherein each of said first and said second fluid receiving receptacles and each of said first and said second fluid input channels has a diameter, the diameters of each of said first and said second fluid receiving receptacles being larger than the diameter of each of said first and said second fluid input channels.

8. The fluid mixing and delivery injector recited in claim 1, wherein said common canal has a beveled exit tip located at the distal end of said injector from which the resultant mixture of said first and said second fluids is delivered to the target site.

9. The fluid mixing and delivery injector recited in claim 8, wherein each of said first and said second fluid input channels has a diameter, the diameter of said common canal being larger at the beveled exit tip thereof than the diameter of each of said first and said second fluid input channels.

10. A fluid mixing and delivery system comprising:
first and second syringes within which first and second fluids to be mixed together are located; and
a fluid injector having a proximal end at which to receive the first and second fluids and a distal end at which the first and second fluids are mixed together and the resultant mixture is delivered to a target site, said fluid injector including:
first and second fluid receiving receptacles located at said proximal end within which said first and second syringes are respectively received for supplying thereto the first and second fluids under pressure;
first and second fluid input channels lying in fluid communication with respective ones of said first and second fluid receiving receptacles so as to receive the first and second fluids under pressure from said first and said second fluid receiving receptacles; and
a common canal located at the distal end of said injector and lying in fluid communication with each of said first and second fluid input channels so that the first and the second fluids within said first and second fluid input channels are introduced to one another and mixed together within said common canal such that the mixture flows through said common canal to be delivered to the target site, each of said first and said second fluid receiving receptacles, said first and said second fluid input channels, and said common canal having a diameter, the diameter of each of said first and second fluid input channels being smaller than the diameter of each of said first and said second fluid receiving receptacles and also being smaller than the diameter of said common canal.

11. The fluid mixing and delivery system recited in claim 10, wherein the diameter of the common canal of said fluid injector increases from narrow to wide in a direction in which the mixture flows therethrough.

12. The fluid mixing and delivery system recited in claim 10, wherein each of the first and second fluid receiving receptacles of said fluid injector is provided with a set of screw threads adapted to bite into and lock said first and second syringes in places within respective ones of said first and second fluid receiving receptacles.

13. The fluid mixing and delivery system recited in claim 10, wherein the first and second fluid input channels of said fluid injector are aligned with one another so that an orthogonal angle is formed therebetween, and each of the first and second fluid input channels and the common canal of said fluid injector has a longitudinal axis, said common canal and said first and said second fluid input channels being positioned so that the longitudinal axis of said common canal and the longitudinal axes of said first and said second fluid input channels are aligned with one another in a Y-shaped configuration.

14. A fluid mixing and delivery injector having a proximal end at which to receive first and second fluids and a distal end at which the first and second fluids are mixed together so that the resultant mixture can be delivered to a target site, said fluid mixing and delivery injector comprising:
first and second fluid receiving receptacles located at the proximal end of the injector at which the first and second fluids to be mixed together are received under pressure;
first and second fluid input channels lying in fluid communication with respective ones of said first and second fluid receiving receptacles so as to receive the first and second fluids under pressure from said first and said second fluid receiving receptacles; and
a common canal located at the distal end of said injector and lying in fluid communication with said first and second fluid input channels, said common canal having at least first and second fluid deflectors located therewithin, said first fluid input channel directing the first fluid against said first fluid deflector and said second fluid input channel directing the second fluid against said second fluid deflector, whereby said first and second fluids are deflected towards one another and mixed together within said common canal such that the resultant mixture flows through said common canal to be delivered to the target site at the distal end of the injector.

15. The fluid mixing and delivery injector recited in claim 14, wherein each of the first and second fluid deflectors has a sloping deflector surface against which said first and second fluids are directed from said first and second fluid input channels so as to be deflected towards one another and mixed together within said common canal.

16. The fluid mixing and delivery injector recited in claim 15, wherein each of the deflector surfaces of said first and second fluid deflectors slopes upwardly in a direction in which the mixture of the first and second fluids flows through said common canal.

17. The fluid mixing and delivery injector recited in claim 15, wherein the first and second upsloping deflector surfaces of said first and second fluid deflectors are aligned with one another so that an orthogonal angle is formed therebetween.

18. The fluid mixing and delivery injector recited in claim 14, wherein said common canal has an exit tip located at the distal end of said injector from which the resultant mixture of the first and second fluids is delivered to the target site, said first and second fluid deflectors lying within said common canal so that the first and second fluids that are deflected towards one another by said first and second fluid deflectors are mixed together within said common canal and the resultant mixture flows through said common canal to said exit tip.

19. The fluid mixing and delivery injector recited in claim 18, wherein said common canal has a diameter that expands in a direction in which the resultant mixture of the first and second fluids flows through said common canal to said exit tip.

20. The fluid mixing and delivery injector recited in claim 19, further comprising first and second fluid canals connected at first ends thereof to respective ones of the first and second fluid input channels and at opposite ends to said common canal so as to direct the first and second fluids from said first and second fluid input channels against the first and second fluid deflectors located within said common canal, each of said first and second fluid canals having a constant diameter that is less than the expanding diameter of said common canal.

21. A fluid mixing and delivery injector having a proximal end at which to receive first and second fluids and a distal end at which the first and second fluids are mixed together so that the resultant mixture can be delivered to a target site, said fluid mixing and delivery injector comprising:

first and second fluid receiving receptacles located at the proximal end of the injector at which the first and second fluids to be mixed together are received under pressure;

first and second fluid input channels lying in fluid communication with respective ones of said first and second fluid receiving receptacles so as to receive the first and second fluids under pressure from said first and said second fluid receiving receptacles; and a common canal located at the distal end of said injector and lying in fluid communication with said first and second fluid input channels, such that said first and second fluids under pressure are angled from said first and second fluid input channels towards one another so as to intersect each other at a collision point within said common canal, whereby the first and second fluids are mixed together and the resultant mixture flows through said common canal to the target site from the distal end of said injector.

22. The fluid mixing and delivery injector recited in claim 21, wherein each of said first and second fluid input channels has an angled wall extending thereacross and an aperture formed through each of said angled walls such that the first and second fluids received under pressure by said first and second fluid input channels are angled towards one another to be mixed together at said collision point within said common canal by way of the apertures formed through said angled walls.

23. The fluid mixing and delivery injector recited in claim 21, wherein the angled walls extending across said first and second fluid input channels slope in an upward direction corresponding to a direction in which the resultant mixture of the first and second fluids flows through said common canal to the target site.

24. The fluid mixing and delivery injector recited in claim 21, wherein said injector has a distal tip at the distal end thereof from which the resultant mixture of the first and second fluids is expulsed to the target site, said common canal being located at and lying in fluid communication with said distal tip.

25. The fluid mixing and delivery injector recited in claim 21, wherein said common canal has a divergent diameter that expands in the same direction in which the resultant mixture of the first and second fluids flows through said common canal.

* * * * *